(12) United States Patent
Cardoso Dias

(10) Patent No.: US 6,503,493 B1
(45) Date of Patent: *Jan. 7, 2003

(54) PROCESS FOR OBTAINING A HAIR CONDITIONING AGENT

(75) Inventor: Lindolfo Cardoso Dias, Rio de Janeiro (BR)

(73) Assignee: Cosme Vieira Nunes, Rio de Janeiro (BR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/372,993

(22) Filed: Aug. 12, 1999

(30) Foreign Application Priority Data

Aug. 18, 1998 (BR) ................................ 9803170

(51) Int. Cl.⁷ .......................... A61K 6/00; A61K 7/00; A61K 7/06
(52) U.S. Cl. ...................................... 424/70.1; 424/401
(58) Field of Search ................................ 424/70.1, 401

(56) References Cited

U.S. PATENT DOCUMENTS

| | | | | |
|---|---|---|---|---|
| 5,472,688 A | * | 12/1995 | Soukup | 424/70.1 |
| 5,496,827 A | * | 3/1996 | Patrick | 514/310 |
| 5,681,554 A | * | 10/1997 | Cannell et al. | 424/70.14 |
| 5,710,177 A | * | 1/1998 | Sauermann et al. | 514/557 |

\* cited by examiner

*Primary Examiner*—Thurman K. Page
*Assistant Examiner*—S. Howard
(74) *Attorney, Agent, or Firm*—Jacobson Holman PLLC

(57) ABSTRACT

An improved process for obtaining a hair conditioning agent which softens, provides brightness and flexibility to the hair, increasing its trend of maintaining the desired hair format; the active ingredients of the conditioning agent are ascorbic acid/pyrogalol, manganese salts, the conditioning agent, in a version, and is being presented to users in the form of a powder, containing, in addition to the active elements of a thickener, which, before being applied by user, is being mixed with water, and, in another version, the material is being offered in the form of a cream, gel or paste to be used directly on the hair, and in both cases other specific action ingredients may be contained in said blend.

6 Claims, No Drawings

PROCESS FOR OBTAINING A HAIR CONDITIONING AGENT

The present invention is related to an improved process for obtaining a hair dressing agent, capable of increasing brightness, softness and flexibility levels, as well as the trend of preserving the desired hair format, without evidencing the problems of known hair dressing agents, involving greenish and/or darkening tints when applied on brown, clair and greyish hair, as well as the characteristic undesirable metallic smell during the hair dying process.

The known technique reveals that hairdressing agents significantly improve both the visual aspect and the physical appearance of hair, submitted to treatment with the above-mentioned hairdressing agent.

The hair dressing technology envisages the occurrence of an encompassing number of formulae for obtaining a hair dressing agent.

As is known by specialists in hairdressing agent technology, processes for obtaining cremes use, in a general way, copper chlorate, ascorbic acid/pyrogallol, ammonium chlorate, soluble starch, etc. However, as has been noted, after the third application of such agents, using copper chlorate, one observe a trend of brown, clair and greyish hair acquiring a "greenish tint" (darkening) due to a copper deposit ($Cu^{+2}$) in strands of hair, in addition to a characteristic unpleasant metallic smell while drying the hair.

In the corresponding request for Letters Patent, an improved process is mentioned, which consists in producing an entirely new type of hair dressing agent, extremely efficient as far as its basic objectives are concerned, such as natural brightness, softness, durability of format of dressed hair, etc., in addition to solving problems of the greenish/dark tint and unpleasant smell, as mentioned above, and a basically safe product is obtained, which does not attack the scalp surface, with which the cream enters in contact at the time of its application and remaining thereon for a large period of time.

The active ingredients of the formula applied in the improved process of the present invention are ascorbic acid and manganese salts.

Ascorbic acid ($C_6H_8O_6$) is a crystalline and white vitamin, found in fruits, especially in citric fruits and in some green leaf vegetables, and is also called vitamin "C".

The agent originated from the process of the present invention is offered to users in a packing, in powdered form, which, in addition to active ingredients (effectively acting to obtain desired effects), contains a thickening material which, before its application by a user, is mixed with water.

Another presentation of the dressing agent to the user, resulting from the improved process of the present invention, is evidenced in the form of a convenient gel, paste or cream, which may be used directly in this condition by users who intend to condition their hair.

The formulations of the improved process of the present invention may also include (without changing the inventive value of the improved process) a surfactant agent, a wetting component and functional equivalents or similar items, in addition to other compounds used in treating and hair modeling, such as a quaternary salt, a dye, a relaxing agent, etc.

With the purpose of offering a more encompassing insight on the improved process for obtaining hair conditioning agents, pursuant to the present invention, subsequently some examples of formulae will be described, which may be accomplished in order to attain the objectives of the improved process of the invention, i.e. an improved process capable of generating an efficient hair conditioning agent, without the problems found in the earlier art, and without restricing the invention with the problems.

It should, however, be pointed out that formulae are presented herein solely for exemplification and clarification and are not, in any way, restrictive of the invention.

EXAMPLE 1

In an adequate recipient, one triturates 1 g manganese chlorate, 20 g ascorbic acid, 5 g ammonium chlorate and 15 g soluble starch. The powder thus obtained, mixed with water and applied over the hair, originates a permanent brightness, softness and flexibility, of an essentially improved nature than the usual hair conditioning agents of the art.

EXAMPLE 2

For an adequate recipient, one dissolves 15 g of citric acid, 5 g of ascorbic acid, 0.7 g of manganese chlorate, and 5 g of ammonium chlorate in 150 ml of water, adding 25 g of carboxymethyl cellulose; the several components are agitated until a homogeneous paste is obtained, which is applied over the hair. Resulting brightness, softness and flexibility of the hair are superior to results obtained by application of traditional hair conditioning agents available on the market.

EXAMPLE 3

For an adequate recipient, one dissolves 3 g of ascorbic acid, 5 g of sodium thiosulfate, 15 g of citric acid, 0.7 g of manganese chlorate and 5 g of ammonium chlorate in 150 ml of water; one adds 25 g of pre-gelled starch and agitates the resulting blend until a homogeneous cream is obtained. Hair treated with said cream, washed and then dried in a desired format (wave-like or smooth) evidences brightness, softness and flexibility, featuring the improved process of the present invention, in addition to maintaining its format permanently without evidencing problems encountered in earlier art.

EXAMPLE 4

In an adequate recipient, one dissolves 20 g ascorbic acid, 0,7 g manganese chlorate, 5 g zinc chlorate, 3 g sodium bicarbonate, starch and water. The product obtained is within the utilization standards as mentioned above, evidencing all advantages of the products mentioned earlier.

One thus obtains, with the improved process of the present invention, hair conditioning agents which no longer evidence problems of producing a greenish/darkening tint of conventional hair conditioning agents, using copper chlorate, and thus also avoiding the characteristic undesirable metallic smell of known hair conditioning agents.

I claim:

1. A hair conditioning composition comprising active ingredients and, optionally, a hair conditioning auxiliary agent, wherein the active ingredients consist essentially of ascorbic acid and a maganese salt, and wherein the auxiliary agent comprises ammonium chlorate and soluble starch.

2. A hair conditioning composition comprising active ingredients and, optionally, a hair conditioning auxiliary agent, wherein the active ingredients consist essentially of ascorbic acid and a maganese salt, and wherein the auxiliary agent comprises citric acid, ammonium chlorate, carboxymethyl cellulose and water.

3. A hair conditioning composition comprising active ingredients and, optionally, a hair conditioning auxiliary agent, wherein the active ingredients consist essentially of ascorbic acid and a maganese salt, and wherein the auxiliary agent comprises sodium thiosulfate, citric acid, manganese chlorate, starch and water.

4. A hair conditioning composition comprising active ingredients and, optionally, a hair conditioning auxiliary agent, wherein the active ingredients consist essentially of ascorbic acid and a maganese salt, and wherein the auxiliary agent comprises zinc chlorate, sodium bicarbonate, starch and water.

5. A composition of claim 1 in dry powder form.

6. A hair conditioning composition of claim 4 aqueous form.

* * * * *